US00PP36215P2

(12) United States Plant Patent
Cole, III

(10) Patent No.: US PP36,215 P2
(45) Date of Patent: Oct. 22, 2024

(54) ***BUXUS* PLANT NAMED 'LP 03'**

(50) Latin Name: *Buxus microphylla*
Varietal Denomination: LP 03

(71) Applicant: Little Plants, LLC, Pipestem, WV (US)

(72) Inventor: Norman Hamilton Cole, III, Pipestem, WV (US)

(73) Assignee: LITTLE PLANTS, LLC, Pipestem, WV (US)

( * ) Notice: Subject to any disclaimer, the term of this patent is extended or adjusted under 35 U.S.C. 154(b) by 0 days.

(21) Appl. No.: 18/400,371

(22) Filed: Dec. 29, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP24,703 P3 7/2014 Cole, III

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of *Buxus microphylla* plant, referred to by its cultivar name, 'LP 03', is disclosed. The new variety provides dark green leaf color, which is retained year-round. Excellent winter hardiness to at least USDA Zone 5 is exhibited. The growth habit is compact and rounded, which is wider than tall. The new variety is well suited for providing attractive ornamentation in the landscape.

1 Drawing Sheet

Latin name of genus and species of plant claimed: *Buxus microphylla.*

Variety denomination: 'LP 03'.

BACKGROUND OF THE INVENTION

The new variety of *Buxus microphylla* plant was discovered as a whole plant mutation in a production stock block of *Buxus microphylla* 'Little Missy' (U.S. Plant Pat. No. 24,703) in Pipestem, West Virginia during summer 2019.

The new variety has been found to undergo asexual propagation by terminal hardwood stem cuttings. Asexual propagation by terminal stem cuttings in Pipestem, West Virginia has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Buxus microphylla* plant of the present invention:

(a) displays dark green leaf color, which is retained year-round,
(b) exhibits excellent winter hardiness to at least USDA Zone 5, and
(c) provides a compact, rounded growth habit, which is wider than tall.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished similar varieties that are commercially available. The most similar in comparison to the new cultivar is the 'Little Missy' variety (i.e., the parent variety). The new variety of the present invention can readily be distinguished at least because plants of the new variety have a faster growth rate, larger and more rounded leaves, and thicker more woody stems compared to plants of the 'Little Missy' variety. In particular, the mature leaf size of the 'Little Missy' variety is approximately 1.6 cm in length and 1.0 cm in width, whereas the mature leaf size of the new variety is larger, approximately 2.0 cm in length and typically between 1.0 cm to 2.0 cm in width. As another example, the new variety of the present invention can readily be distinguished from the 'Faulkner' variety (not patented) in at least plants of the new variety are more compact in size, have a shorter internode length, a denser growth habit, and a finer root system compared to plants of 'Faulkner'.

The new variety has been named 'LP 03'.

BRIEF DESCRIPTION OF THE PHOTOGRAPH

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'LP 03' variety. The photographed plant was approximately five-years-old and growing in a production field in Pipestem, West Virginia in February 2023.

Drawing—illustrates a specimen of the plant displaying the overall growth and habit.

DETAILED BOTANICAL DESCRIPTION

The chart used in the identification of the colors is that of The Royal Horticultural Society (The R.H.S. Colour Chart), 2015 edition, London, England. The terminology which precedes reference to the chart has been added to indicate the corresponding color in more common terms and The R.H.S. Colour Chart designation used herein represents the closest color observed on the majority of the specified botanical feature. The color values were determined in September 2023 under natural light conditions in Cochranville, Pennsylvania. The description is based on the observation of plants approximately five months of age growing in a 3-gallon container in a nursery setting in Cochranville, Pennsylvania. Measurements and numerical values represent averages of typical plants.

Botanical classification: *Buxus microphylla* cultivar LP 03.

Propagation:

*Type cutting*.—Terminal stem cuttings.

*Time to initiate roots during the fall*.—Approximately 30 to 45 days on average.

*Root description*.—White, medium thickness, fibrous.

*Rooting habit*.—Moderate branching and density.

Plant:

*Habit*.—Evergreen shrub, moderately vigorous, compact, rounded growth shape that is wider than tall.

*Commercial crop time*.—Approximately 14-16 months from a rooted cutting to finish in a 3-gallon pot on average.

*Size*.—Approximately 36.0 cm in height from soil level to top of plant plane on average; and approximately 32.0 cm in width on average.

Branches:

*Branching habit*.—Freely branching, pinching enhances branching.

*Quantity of main branches per plant*.—Approximately 11 on average.

*Shape*.—Rounded.

*Strength*.—Very strong.

*Size*.—Length: approximately 25.0 cm on average. — diameter: approximately 8.0 mm on average. — length of central internode: approximately 1.0 cm on average.

*Texture*.—Young stems: glabrous. — mature stems: woody.

*Color*.—Young stems: commonly Green Group 143B. — mature stems: commonly Greyed-Orange Group 165C.

Foliage:

*Number of leaves*.—Typically between 10 to 14 per lateral branch.

*Fragrance*.—Somewhat grass-like when crushed.

*Form*.—Simple.

*Arrangement*.—Opposite.

Leaves:

*Shape*.—General: ovate. — margin: entire. — apex: rounded. — base: obtuse.

*Venation*.—Pattern: pinnate.

*Size*.—Length of juvenile leaf: approximately 1.1 cm on average. — width of juvenile leaf: approximately 7.0 mm on average. — length of mature leaf: approximately 2.0 cm on average. — width of mature leaf: typically between 1.0 cm to 2.0 cm.

*Texture*.—Upper and lower surfaces: glabrous.

*Color*.—Upper surface of young foliage: commonly Green Group 143A with venation of Green Group 143C. — lower surface of young foliage: commonly Green Group 143C with venation of Yellow-Green Group 146D. — upper surface of mature foliage: commonly Green Group NN137A with venation of Yellow-Green Group 147B. — lower surface of mature foliage: commonly Yellow-Green Group 146B with venation of Yellow-Green Group 147C.

*Petiole*.—Length: approximately 2.0 mm on average. — width: approximately 1.0 mm on average. — texture: glabrous. — color: commonly Yellow-Green Group 146B.

Inflorescence: None observed to date.

Seed and fruit: None have been observed to date.

Development:

*Hardiness*.—USDA Zone 5.

*Tolerance to disease and pest*.—Not observed to date.

The new 'LP 03' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Buxus microphylla* plant named 'LP 03' characterized by the following combination of characteristics:

(a) displays dark green leaf color, which is retained year-round, (b) exhibits excellent winter hardiness to at least USDA Zone 5, and (c) provides a compact, rounded growth habit, which is wider than tall; substantially as herein shown and described.

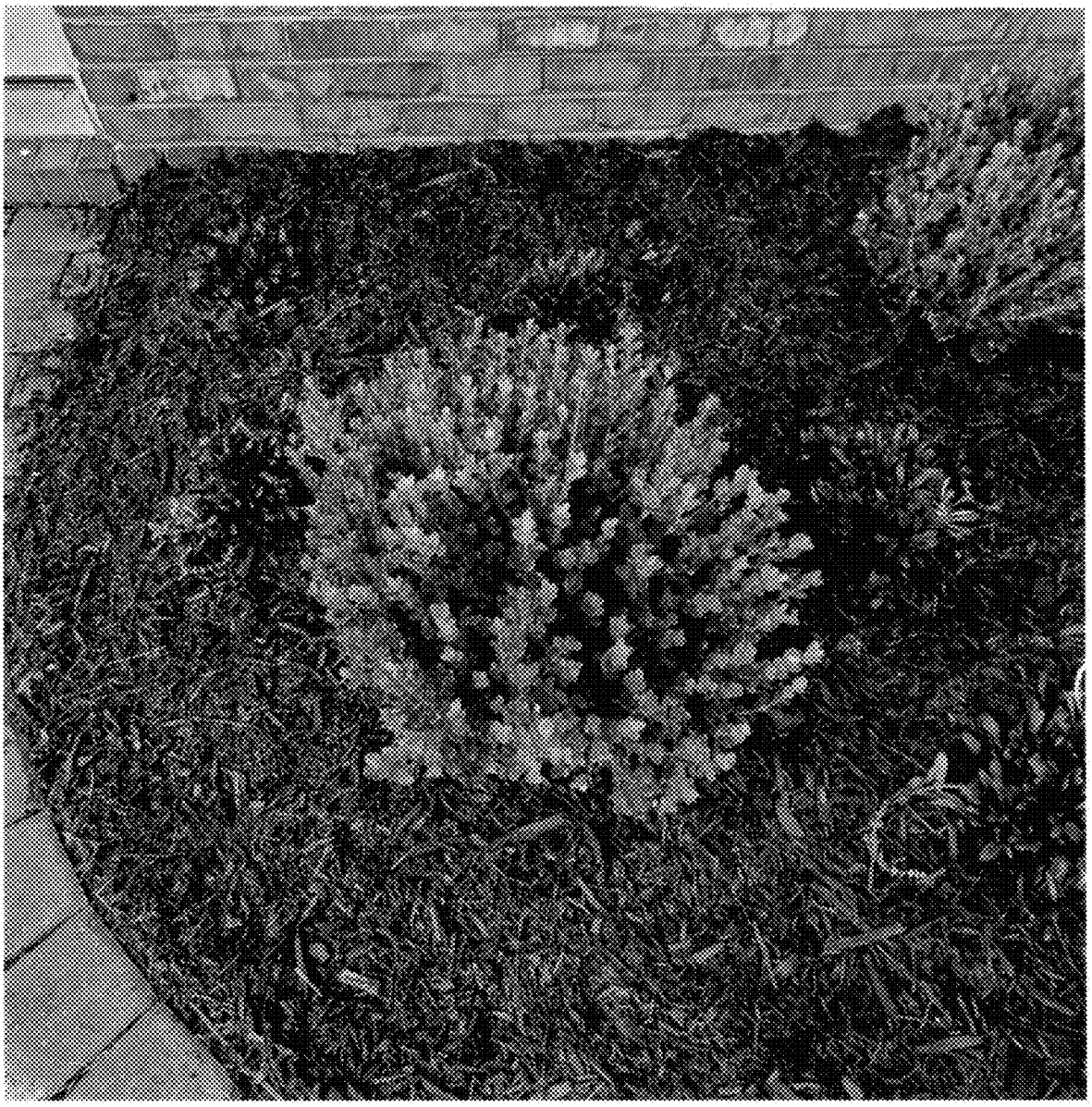

* * * * *